(12) United States Patent
Wooldridge (10) Patent No.: US 8,622,231 B2
(45) Date of Patent: Jan. 7, 2014

(54) STORAGE CONTAINERS FOR TEST ELEMENTS

(75) Inventor: Scott Wooldridge, Carmel, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 577 days.

(21) Appl. No.: 12/555,957

(22) Filed: Sep. 9, 2009

(65) Prior Publication Data

US 2011/0056951 A1  Mar. 10, 2011

(51) Int. Cl.
*B65D 6/00* (2006.01)

(52) U.S. Cl.
USPC ................................ 220/495.01; 220/87.1

(58) Field of Classification Search
USPC ................... 220/495.01, 87.1; 422/500, 562; 96/135, 154
See application file for complete search history.

(56) References Cited

U.S. PATENT DOCUMENTS

| | | | |
|---|---|---|---|
| 2,842,223 A * | 7/1958 | Zall ............................... | 502/404 |
| 3,800,515 A | 4/1974 | Asker et al. | |
| 4,911,344 A | 3/1990 | Kahler | |
| 5,520,230 A | 5/1996 | Sumner, III | |
| 5,673,493 A * | 10/1997 | Kazakis et al. .................... | 34/80 |
| 5,723,085 A | 3/1998 | Abrams et al. | |
| 5,911,937 A | 6/1999 | Hekal | |
| 6,080,350 A | 6/2000 | Hekal | |
| 6,130,263 A | 10/2000 | Hekal | |
| 6,378,702 B1 | 4/2002 | Kintzig | |
| 6,497,845 B1 | 12/2002 | Sacherer | |
| 6,534,017 B1 | 3/2003 | Bottwein et al. | |
| 6,682,704 B2 | 1/2004 | Bottwein et al. | |
| D487,594 S | 3/2004 | Alscher et al. | |
| D491,313 S | 6/2004 | Schrott | |
| D527,898 S | 9/2006 | Tavone | |
| 7,213,720 B2 | 5/2007 | Giraud | |
| 7,326,363 B2 | 2/2008 | Faust et al. | |
| 7,597,853 B2 * | 10/2009 | West et al. ..................... | 422/561 |
| 2005/0284836 A1 * | 12/2005 | Majoor et al. ................ | 215/254 |
| 2006/0210203 A1 * | 9/2006 | Gzybowski ..................... | 383/64 |

FOREIGN PATENT DOCUMENTS

| | | |
|---|---|---|
| EP | 0 454 967 A2 | 3/1991 |
| EP | 2 031 389 A1 | 3/2009 |
| WO | WO 96/39343 A1 | 12/1996 |

* cited by examiner

*Primary Examiner* — Stephen Castellano
(74) *Attorney, Agent, or Firm* — Krieg DeVault LLP (57) ABSTRACT

A container includes an external housing having a sidewall extending between a first end and a second end, and an internal chamber extending between the first and second ends and surrounded by the sidewall. The container includes a sleeve member in the internal chamber. The sleeve member may include corrugated desiccant in communication with the internal chamber, or a porous member to maintain desiccant between the internal chamber and the sidewall. The container may also include at least one component in the internal chamber, such as a test element, for use with a biosensor. Other embodiments include unique methods, systems, kits, assemblies, equipment, and/or apparatus which are related to containers including one or more desiccants or desiccant materials.

40 Claims, 9 Drawing Sheets

STORAGE CONTAINERS FOR TEST ELEMENTS

BACKGROUND

As the number of patients suffering from diabetes and similar medical conditions increases, self-monitoring of blood glucose wherein the patient monitors his or her blood glucose levels has become a common practice. The purpose of monitoring the blood glucose level is to determine the concentration level and then to take corrective action, based upon whether the level is too high or too low, to bring the level back within a normal range. The failure to take corrective action can have serious medical implications. Glucose monitoring is a fact of everyday life for diabetic individuals. Failure to test blood glucose levels properly and on a regular basis can result in serious diabetes-related complications, including cardiovascular disease, kidney disease, nerve damage and blindness.

A number of biosensors, such as glucose meters, are currently available that permit an individual to test the glucose level in a small sample of blood. Many of the meter designs currently available make use of a disposable test element which in combination with the meter measures the amount of glucose in the blood sample electrochemically or optically. In current glucose meters, the information displayed as a consequence of a successful blood glucose measurement is the respective blood glucose value, typically shown in mg/dL or mmol units, and perhaps the time and date the measurement was performed. This information in combination with calculation of planned or known intake of carbohydrates or planned or known activities and knowledge of other situational or individual factors is in most cases sufficient to allow diabetics to adjust or derive their dietary intake and/or an immediate dose of insulin to inject to control blood glucose level on the short-term. Also, in case of low glucose values, diabetics can detect the need for intake of sugar to avoid hypoglycemia.

The disposable test elements are typically highly sensitive to environmental conditions. Exposure to humidity in particular can stress a test element to the extent that it is incapable of providing an accurate test. Failsafes and corrections are typically implemented in measurement methods performed by meters corresponding to the particular test element. However, avoiding the adverse environmental conditions altogether is a better way to ensure more accurate test results. In order to avoid such conditions, test elements can be packaged and distributed in containers configured to prevent ingress of moisture from humidity or other sources. In some containers, desiccant material is incorporated somehow within the container, such as in the lid or cap of the container, or an insert that is left in the container with the test elements. However, it is a constant challenge to provide a desiccant material that provides optimum effectiveness. For example, a container having one type of desiccant may be effective during winter months but may not be during summer months, depending on the desiccant material's capacity to absorb and retain environmental moisture. This capacity is itself dependent on several other factors, such as shape, size, and materials.

Given the ramifications of accurate recording, reporting and analyzing of blood glucose measurements, improvements in the containers for packaging and distributing test elements used to meter blood glucose are desired.

SUMMARY

A container includes an internal chamber in communication with one or more desiccants and/or desiccant materials. In one form, the one or more desiccants and/or desiccant materials are arranged such that the surface area of the one or more desiccants and/or desiccant materials in communication with the internal chamber is increased, thereby resulting in greater moisture control within the internal chamber and reducing the likelihood of moisture contamination of any items positioned therein. In one form, wherein test elements for use with a biosensor, such as a blood glucose meter, are positioned in the internal chamber, the reduced likelihood of moisture contamination also reduces the likelihood of error in tests performed with the test elements, as testing accuracy can be adversely affected by moisture contamination of the test elements, among other things.

In one aspect, a container includes an external housing including a sidewall extending between a first end and a second end, and an internal chamber extending between the first and second ends and surrounded by the sidewall. The container also includes a corrugated desiccant in communication with the internal chamber. The desiccant extends along and lines the sidewall of the container.

In one refinement of the aspect, the external housing includes an opening at the first end and a support surface at the second end which encloses the internal chamber at the second end.

In yet another refinement of the aspect, the desiccant comprises a sleeve member removably positionable in the internal chamber and formed of a desiccant material.

In still another refinement of the aspect, the sleeve member is sized and shaped to substantially correspond in size and shape to the internal chamber.

In another refinement of the aspect, the external housing is resiliently flexible.

In another refinement of the aspect, the sidewall includes oppositely positioned first and second portions extending substantially parallel to one another at the first end.

In still another refinement of the aspect, the first and second portions of the sidewall at the first end are releasably engageable with one another to close the internal chamber.

In another refinement of the aspect, the container further includes at least one component for use with a biosensor.

In yet another refinement of the aspect, the at least one component includes a plurality of test elements.

In still another refinement of the aspect, the test elements include a plurality of test strips.

In another refinement of the aspect, the test strips are coupled together in a unitary arrangement wherein the test strips are individually removable from the arrangement.

In another aspect a container includes an external housing extending between a first end and a second end, and a sidewall surrounding an internal chamber. The container also includes a first desiccant including a corrugated sleeve member removably positioned in the internal chamber and formed of a desiccant material. The corrugated sleeve member extends along a longitudinal axis and is generally sized and shaped to substantially correspond in size and shape to the internal chamber as defined by the sidewall.

In one refinement of the aspect, the corrugated sleeve member includes a hollow interior for receiving one or more items stored in the container.

In another refinement of the aspect, the corrugated sleeve member includes a plurality of corrugations extending along the longitudinal axis.

In another refinement of the aspect, the container further includes a porous sleeve member positioned in the hollow interior of the corrugated sleeve member.

In yet another refinement of the aspect, the porous sleeve member includes a hollow interior for receiving the one or more items stored in the container.

In still another refinement of the aspect, the porous sleeve member includes a plurality of openings extending through a sidewall surrounding the hollow interior.

In another refinement of the aspect, the container further includes a second desiccant positioned between the porous sleeve member and the corrugated sleeve member.

In another refinement of the aspect, the desiccant comprises a particulate material.

In still another refinement of the aspect, the container further includes an opening extending through the first end of the external housing and a cap member structured to removably cover the opening coupled to the external housing adjacent to the first end.

In another refinement of the aspect, the container further includes at least one component for use with a biosensor.

In another refinement of the aspect, the at least one component includes a plurality of test elements.

In yet another refinement of the aspect, the test elements comprise test strips.

In still another aspect, a container includes an external housing including a sidewall extending between a first end and a second end. The container also includes a storage chamber for receiving one or more items stored in the container. The storage chamber extends between the first and second ends and is partially defined by a porous surface including a plurality of apertures extending therethrough. The container also includes a first desiccant positioned between the storage chamber and the sidewall of the external housing, and the plurality of apertures facilitates communication between the storage chamber and the first desiccant through the porous surface.

In one refinement of the aspect, the sidewall of the external housing surrounds an internal chamber and the porous surface is positioned on an elongate sleeve member removably positioned in the internal chamber, and the elongate sleeve member includes a hollow interior defining the storage chamber.

In another refinement of the aspect, the elongate sleeve member and the first desiccant extend between the first and second ends of the external housing.

In another refinement of the aspect, the first desiccant includes a corrugated sleeve member formed of a desiccant material, and the corrugated sleeve member extends along a longitudinal axis between the first and second ends of the external housing.

In yet another refinement of the aspect, the corrugated sleeve member includes a hollow interior for receiving the elongate sleeve member.

In still another refinement of the aspect, the corrugated sleeve member includes a plurality of corrugations extending along the longitudinal axis.

In another refinement of the aspect, the container further includes a second desiccant positioned between the storage chamber and the sidewall of the external housing.

In another refinement of the aspect, the second desiccant is positioned between the elongate sleeve member and the corrugated sleeve member.

In still another refinement of the aspect, the second desiccant comprises a particulate material.

In another refinement of the aspect, the first desiccant comprises a particulate material.

In another refinement of the aspect, the container further includes at least one component for use with a biosensor.

In yet another refinement of the aspect, the at least one component includes a plurality of test elements.

In another refinement of the aspect, the test elements include test strips.

In yet another aspect, a desiccant liner includes a body defining a hollow interior and including a cross sectional dimension. The body is configured to facilitate adjustability of the cross sectional dimension and conformity with an internal chamber of a plurality of alternatively sized and shaped containers.

In one refinement of the aspect, the body extends along a longitudinal axis between a first end and a second end and includes a plurality of corrugations extending along the longitudinal axis.

In another refinement of the aspect, the body is foldable along the corrugations to adjust the cross sectional dimension.

In yet another refinement of the aspect, the cross sectional dimension corresponds to external dimension measured laterally across the body.

In still another refinement of the aspect, the liner is positioned in and lines the internal chamber of one of the plurality of containers and the cross sectional dimension includes an inserted configuration. In the inserted configuration, the cross sectional dimension is greater than the cross sectional dimension in an insertion configuration when said body is being inserted into the internal chamber.

Another aspect of the present application is a unique container for reducing the likelihood of moisture contamination of one or more items stored in the container. In one aspect, the container reduces the likelihood of moisture contamination of test elements used for testing and monitoring blood glucose levels of a diabetic. Other aspects include unique methods, systems, devices, kits, assemblies, equipment, and/or apparatus related to storage containers.

Further aspects, embodiments, forms, features, benefits, objects, and advantages shall become apparent from the detailed description and figures provided herewith.

DETAILED DESCRIPTION OF THE ILLUSTRATED EMBODIMENTS

For purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In order to control and more effectively adjust the therapy, level of activity and lifestyle to achieve optimum glycemic control, diabetics need to measure blood glucose levels on a regular basis. Similarly, diabetics rely on the accuracy of these blood glucose level measurements to properly develop and execute diabetes management plans. Several factors can contribute to inaccuracies and deficiencies in these blood glucose level measurements. For example, contamination of test elements used with a biosensor, such as a blood glucose meter, can lead to false and/or inaccurate blood glucose level measurements. In one particular form, exposure of the test elements to moisture before use with the biosensor can lead to result-affecting contamination. Various embodiments of the present application are related to a desiccant and/or dessicant material for use with a test element container that addresses these and other aspects. In one embodiment, a container includes an internal chamber in communication with one or more desiccants and/or desiccant materials. In one form, the one or more desiccants and/or desiccant materials are arranged such that the surface area of the one or more desiccants and/or desiccant materials in communication with the internal chamber is increased, thereby resulting in greater moisture control within the internal chamber and reducing the likelihood of moisture contamination of any items, such as test elements, positioned therein. As used herein, the term "desiccant" when used alone generally refers to a drying or moisture control substance or agent, while the term "desiccant material" generally refers to a material suitable for performing drying and/or moisture control.

Figure 1:
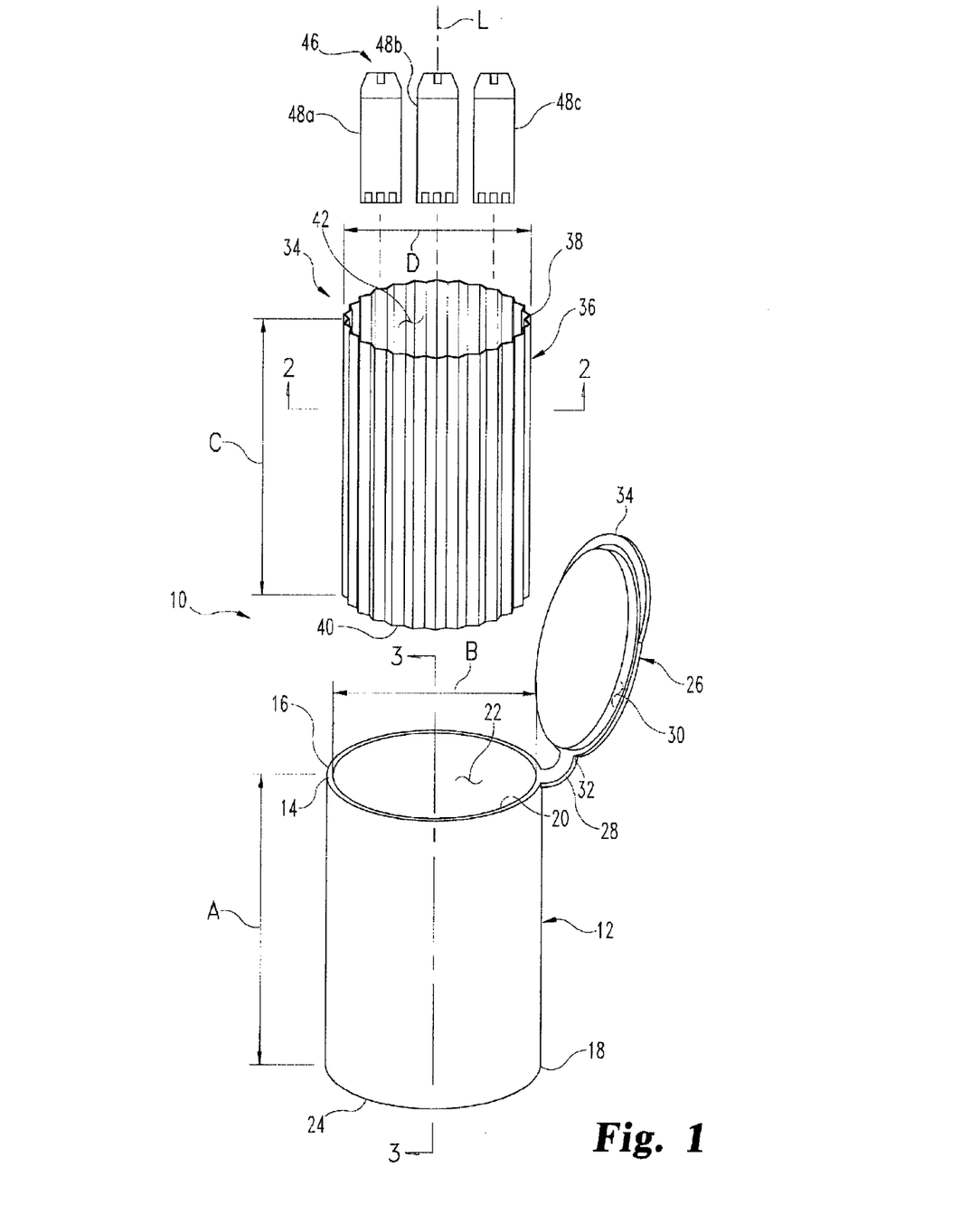
FIG. 1 is an exploded, perspective view of one embodiment of a storage container including a desiccant.
Figure 1A:
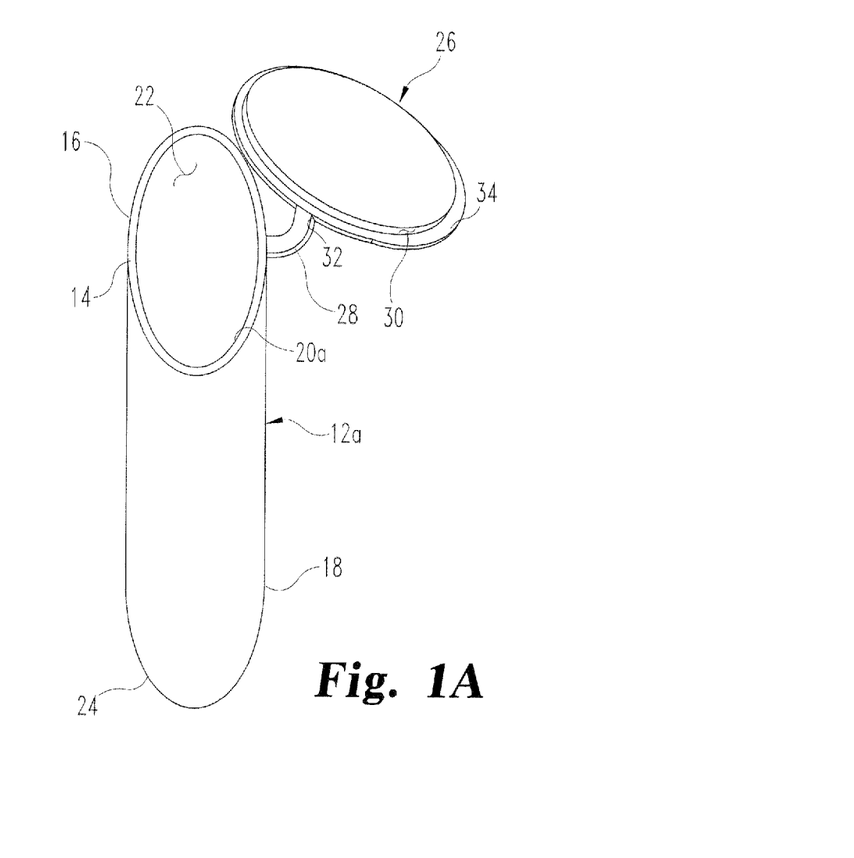
FIG. 1A is a perspective view of an alternatively configured housing suitable for use in the embodiment of FIG. 1.

Referring now generally to FIG. 1, various aspects of one embodiment of a container 10 are illustrated. Container 10 includes an external housing 12 having at least one longitudinal sidewall 14 extending along a longitudinal axis L and having a length A between a first end 16 and a second end 18. In the illustrated embodiment, external housing 12 has a generally cylindrical outer profile and sidewall 14 circumferentially or laterally surrounds an internal chamber 20 that extends between first end 16 and second end 18. Similarly, internal chamber 20 includes a hollow cylindrical shape that generally corresponds to the outer profile of external housing 12. It should be appreciated however that in alternative forms one or both of external housing 12 and internal chamber 20 could have other shapes, including non-circular shapes and polygonal shapes, such as oval, rectangular, triangular or square configurations, just to provide a few possibilities. For example, with reference to FIG. 1A, where like numerals refer to like features described with respect to container 10, an external housing 12a that has a generally oval outer profile and an internal chamber 20a that has a hollow oval shape generally corresponding to the outer profile of external housing 12a are illustrated. With reference again to container 10 illustrated in FIG. 1, it also includes an opening 22 extending through first end 16 of external housing 12 and providing access to internal chamber 20. Opposite opening 22, a bottom or support surface 24 extends between sidewall 14 and provides support for items positioned in internal chamber 20, while also enclosing internal chamber 20 at second end 18.

In the illustrated embodiment, container 10 also includes a cap member 26 coupled to external housing 12 adjacent first end 16 via a coupling element 28, although in other alternative, non-illustrated forms it is contemplated that cap member 26 may not be coupled to external housing 12, or may be omitted entirely or replaced by an alternative arrangement for closing internal chamber 20. Coupling element 28 is generally flexible and facilitates movement of cap member 26 relative to external housing 12. An annular projection 30 extends from the bottom side of cap member 26 and is generally structured to sealingly engage with the internal surface of sidewall 14 and close internal chamber 20 at first end 16. For example, annular projection 30 may be provided with a diameter that is the same or substantially similar to an internal dimension, which in the illustrated form is diameter B, of internal chamber 20. When projection 30 is positioned in internal chamber 20 and engages with sidewall 14, an annular flat portion 32 of cap member 26 lies against the end of sidewall 14 at first end 16 of external housing 20. Cap member 26 also includes a projection 34 extending laterally beyond flat portion 32 along one side thereof. When cap member 26 is engaged with external housing 12, projection 34 extends outwardly from sidewall 14 thereby allowing a user to engage cap member 26 and move it away from first end 16 of external housing 12 to provide access to internal chamber 20.

While not illustrated in FIG. 1, it should be appreciated that one or both of sidewall 14 and projection 30 could be provided with a sealing member, such as an o-ring, gasket, interlocking members, or other configuration. It should also be appreciated that cap member 26 may be sized and shaped to correspond with alternative, non-illustrated sizes and shapes of external housing 12. Additional variations in the arrangement between cap member 26 and external housing 12 are also contemplated. For example, in one non-illustrated form, cap member 26 can be configured to extend around first end 16 and along the exterior of sidewall 14 toward second end 18. Cap member 26 may be configured to engage sidewall 14 with a threaded, twist lock, bayonet lock, friction fit, or other suitable engagement relationship. In another form, cap member 26 can include an opening extending therethrough and a closing member cooperating with the opening such that one or more items can be removed from internal chamber 20 without disengaging cap member 26 from external housing 12. The closing member can be in the form of a plug, valve, or other suitable closeable access device.

Figure 2:
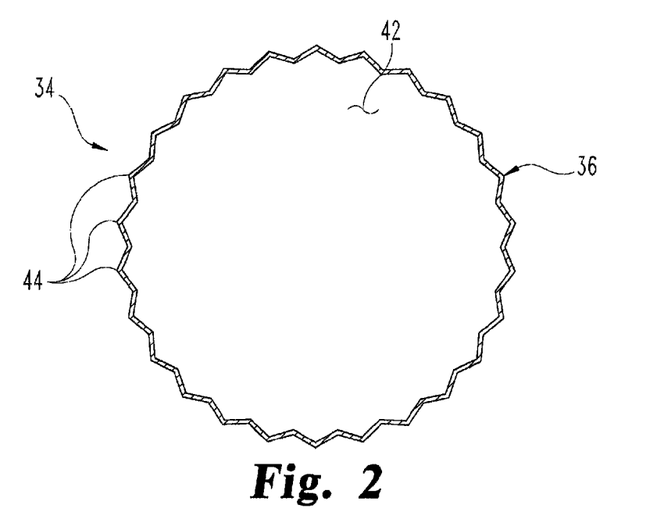
FIG. 2 is a cross-section view of the desiccant illustrated in FIG. 1 taken along view line 2-2.
Figure 3:
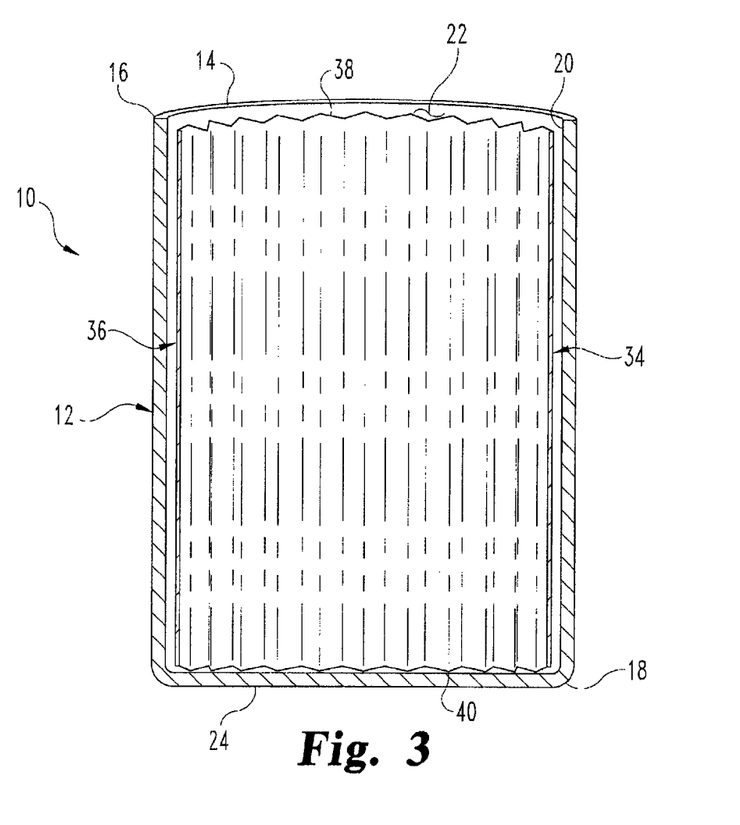
FIG. 3 is cross-section view of the container of FIG. 1 with the desiccant positioned therein and taken along view line 3-3.

Container 10 also includes a desiccant 34 in the form of a sleeve member 36 extending along longitudinal axis L between a first end 38 and a second end 40. In one or more non-illustrated forms however, it is contemplated that container 10 may also include another desiccant in addition to desiccant 34. For example, in one particular form, sidewall 14 of external housing 12 could be formed from a desiccant entrained polymer material, although other configurations are contemplated. Sleeve member 36 includes a hollow interior 42 that extends between and opens at first and second ends 38, 40. In one non-illustrated form however, sleeve member 36 could be provided with a bottom surface that encloses hollow interior 42 at second end 40. As illustrated in FIGS. 2 and 3, sleeve member 36 also includes a length C between first end 38 and second end 40 and an external dimension, which in the illustrated form is diameter D, which substantially correspond to length A of external housing 12 and the internal dimension (diameter B in the illustrated form) of internal chamber 20, respectively, such that sleeve member 36 substantially corresponds in size and shape to internal chamber 20. As illustrated in FIG. 3 for example, sleeve member 36 is removably positionable in internal chamber 20 such that desiccant 34 extends along and lines the interior surface of sidewall 14 between first and second ends 16, 18 of external housing 12. When sleeve member 36 is positioned in internal chamber 20, hollow interior 42 provides a storage chamber for receiving one or more items stored in container 10. In one or more non-illustrated forms, it is contemplated that sleeve member 36 could be secured in internal chamber 20 by fasteners or adhesives, or could be formed integrally as a monolithic structure with sidewall 14. In another form, sleeve member 36 is configured to achieve a press fit engagement with internal chamber 20, further details of which will be provided below with respect to FIGS. 6 and 7. In still another form, it is contemplated that sleeve member 36 may be retained in internal chamber 20 by a retention ring (not shown), although other alternative configurations for retaining sleeve member 36 in internal chamber 20 are also contemplated.

In the illustrated embodiment, sleeve member 36 is corrugated and includes a plurality of corrugations 44 extending along longitudinal axis L from first end 38 to second end 40. However, alternative arrangements for corrugations 44 are also contemplated. For example, in one non-illustrated form, corrugations 44 may extend orthogonally or obliquely relative to longitudinal axis L. In another non-illustrated embodiment, sleeve member 36 may be provided with corrugations 44 that extend only partially between first end 38 and second end 40. For example, in one form, sleeve member 36 may include one or more non-corrugated portions positioned between one or more corrugated portions. Alternatively, sleeve member 36 may only be corrugated adjacent first end 38 or second end 40, or at intermittent locations along the length of sleeve member 36. In other forms, sleeve member length C is substantially less than length A of external housing 12.

Figures 4, 5:
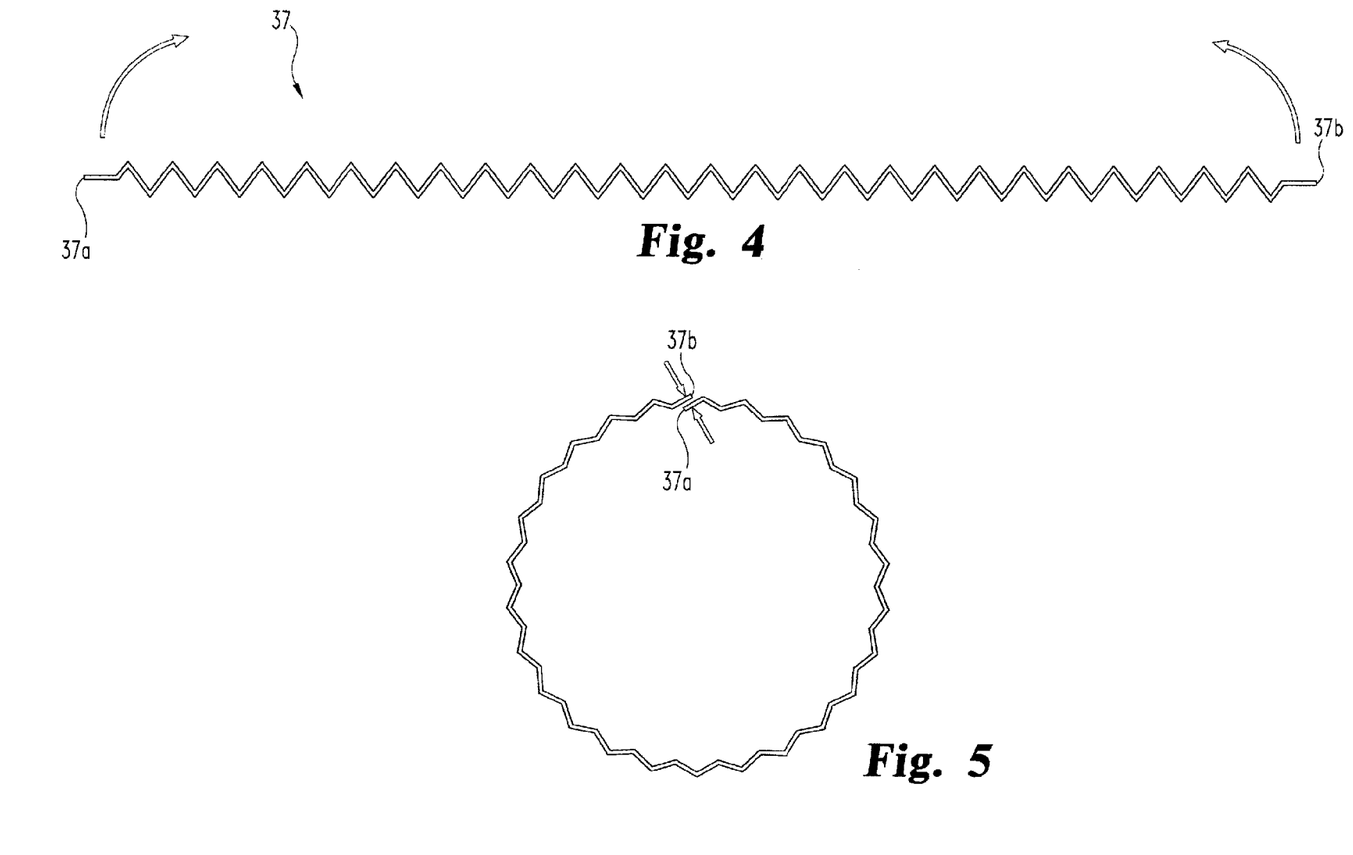
FIG. 4 is a plan view of a corrugated sheet that can be used to make the desiccant illustrated in FIG. 1.
FIG. 5 is a plan view of the corrugated sheet illustrated in FIG. 4 being manipulated to form the desiccant illustrated in FIG. 1.

It is contemplated that sleeve member 36 may be formed by any suitable process. In one non-limiting example, sleeve member 36 may be formed utilizing extrusion methods and processes. Another non-limiting example is illustrated in FIGS. 4 and 5. More particularly, as illustrated in FIG. 4, opposite end portions 37a and 37b of a corrugated sheet 37 may be rotated toward each other to arrive at the arrangement illustrated in FIG. 5 where end portion 37b is positioned above end portion 37a. End portions 37a and 37b may then be joined together in overlapping fashion by taping, gluing, or crimping, just to name a few possibilities, to form sleeve member 36. In an alternative form, it is also contemplated that the ends of end portions 37a and 37b could be connected in an abutting fashion to provide sleeve member 36. Still, it should be appreciated that sleeve member 36 could be formed by other manners as well. For example, in one alternative form, it is contemplated that sleeve member 36 could include an integral structure that is free from any interconnection between opposite ends of a corrugated sheet.

Sleeve member 36 is generally formed from or includes one or more desiccant materials, non-limiting examples of which may include porous paper, cellulosic fiber, a desiccant entrained polymer, porous plastic, molecular sieves, silica gels, clays, starches, calcium sulfate and/or calcium chloride, just to provide a few non-limiting possibilities. In one form, it is contemplated that the desiccating characteristics of sleeve member 36 can be adjusted in relation to the moisture control conditions required in internal chamber 20. For example, in one form it is contemplated that the desiccant material from which sleeve member 36 is formed may be chosen to meet the required moisture control conditions of all or one or more parts of internal chamber 20. In another form, sleeve member 36 may include two or more portions that are formed of separate desiccant materials each having unique drying or moisture control characteristics. For example, in one form, sleeve member 36 may be formed of a first desiccant material adjacent first end 38 that provides a first level of desiccating and a second desiccant material adjacent second end 40 which achieves a second level of desiccating that is different from the first level. In another form, it is contemplated that the material forming sleeve member 36 could include a variable thickness between first end 38 and second end 40. For example, the thickness of the material may taper from first end 38 to second end 40, with sleeve member 36 providing greater desiccating adjacent first end 38 compared to the desiccating provided adjacent to second end 40. In still another form, it is contemplated that the desiccating characteristics of sleeve member 36 can be determined by adjusting the amount of desiccant material it includes. In one particular example of this form, sleeve member 36 may be formed of different amounts of desiccant material along one or more distinct regions to provide corresponding regions of unique desiccating characteristics. However, it should be appreciated that alternative configurations of sleeve member 36 to achieve unique dryness or moisture control conditions are also contemplated.

As illustrated in FIG. 1 for example, a plurality of test elements 46 suitable for use with a biosensor is positionable in hollow interior 42 of sleeve member 36 when sleeve member 36 is positioned in internal chamber 20. It should be appreciated however that other items, in addition to or in lieu of the plurality of test elements 46, may be stored in container 10. In the illustrated form, test elements 46 are provided as electrochemical test strips 48a, 48b, 48c which are useable with a blood glucose meter (not shown) to perform a blood glucose measurement utilizing electrochemical techniques. In one alternative, non-illustrated form, test elements 46 may be provided as test strips used to perform a blood glucose measurement utilizing optical techniques. An example of a test element 46 configured for use with electrochemical techniques is the ACCU-CHEK® Aviva test strip, which is described more fully in U.S. Patent Application Publication No. 2005/0016844, the disclosure of which is hereby incorporated herein by reference in its entirety; and an example of a test element configured for use with optical techniques is the ACCU-CHEK® Compact test strip, which is described more fully in U.S. Pat. No. 7,008,799, the disclosure of which is hereby incorporated herein by reference in its entirety. Each of these exemplary test elements are distributed in the United States by Roche Diagnostics Corporation of Indianapolis, Ind.

Further details and examples of conventional blood glucose meters and related electrical and optical components and their respective measurement techniques are described in U.S. Pat. Nos. 5,352,351; 4,999,482; 5,438,271; 6,645,368; 5,997,817; 6,662,439; RE 36,268; 5,463,467; 5,424,035;

6,055,060; 6,906,802; and 5,889,585; the disclosures of which are hereby incorporated herein by reference in their entireties.

Figure 6:
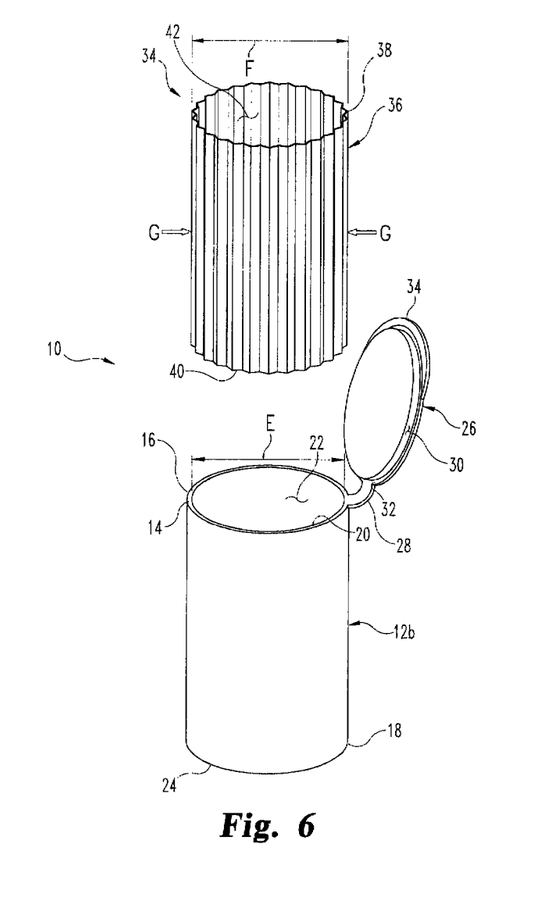
FIG. 6 is an exploded, perspective view of one form of the desiccant illustrated in FIG. 1 relative to another alternatively configured housing.

While not previously described, it should be appreciated that in one or more forms sleeve member 36 can be compressible to facilitate its positioning in the internal chamber of a plurality of alternatively sized and shaped containers. For example, with reference to FIGS. 6 and 7, where like numerals refer to like features described with respect to container 10, an external housing 12b includes a generally cylindrical outer profile and an internal chamber 20b includes a hollow cylindrical shape that generally corresponds to the outer profile of external housing 12b. It should be appreciated however that in alternative forms one or both of external housing 12b and internal chamber 20b could have other shapes, including non-circular shapes and polygonal shapes, such as oval, rectangular, triangular or square shapes, just to provide a few possibilities. As illustrated in FIG. 6, sleeve member 36 includes an initial external dimension F which generally corresponds to a cross sectional dimension taken laterally across sleeve member 36. Initial external dimension F is larger than the internal dimension, which in the illustrated form is diameter E, of internal chamber 20b, although it is contemplated that sleeve member 36 could be used with an internal chamber that is similarly sized or larger than initial external dimension F. To facilitate positioning of sleeve member 36 into internal chamber 20b, an external force indicated by directional arrows G may be applied to compress sleeve member 36, resulting in reduced external dimension H illustrated in FIG. 7. In the illustrated form, it is contemplated that sleeve member 36 may be compressed to provide reduced external dimension H by being folded or bent along one or more of corrugations 44, although alternative configurations for providing sleeve member 36 in a compressible configuration are contemplated.

Figure 7:
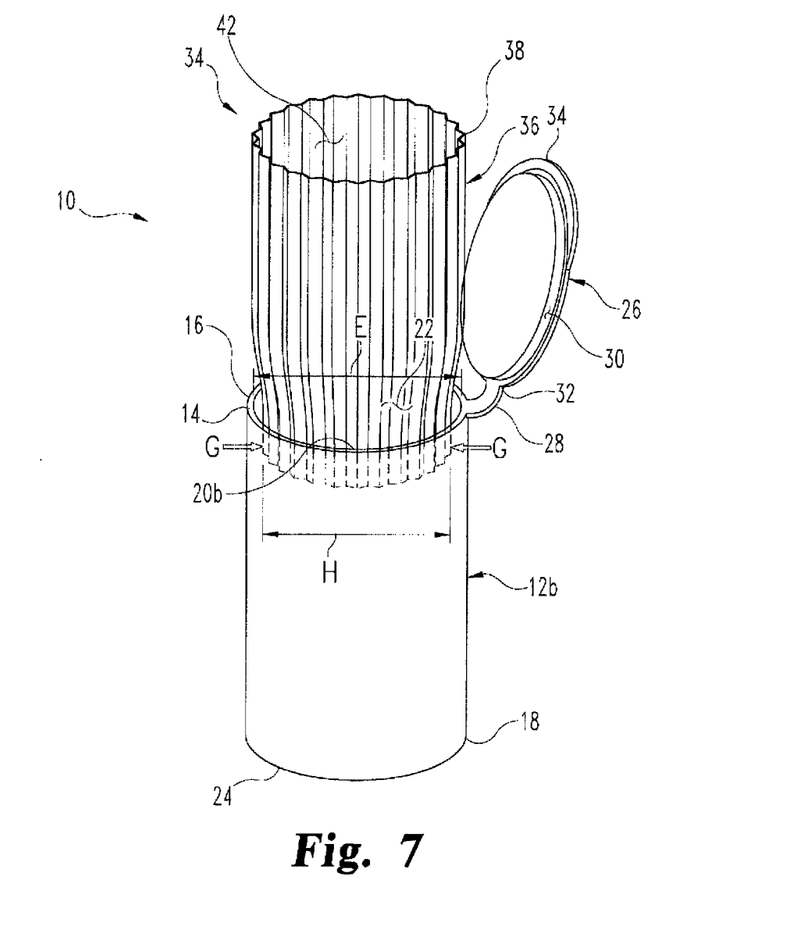
FIG. 7 is a partially exploded, perspective view of the desiccant illustrated in FIG. 6 being positioned into the alternatively configured housing of FIG. 6.

Reduced external dimension H of sleeve member 36 is generally at least slightly smaller than diameter F of internal chamber 20 to allow positioning of sleeve member 36 therein as illustrated in FIG. 7, where sleeve member 36 has been partially inserted into internal chamber 20b. Once sleeve member 36 has been fully positioned in internal chamber 20b and the external forces (indicated by directional arrows G) have been removed therefrom, it resiliently expands to generally conform in size and shape with internal chamber 20b. Similarly, an expansion force along and against internal chamber 20b is created by sleeve member 36 such that sleeve member 36 is securely retained in internal chamber 20b. However, it should be appreciated that sleeve member 36 may also be retained in internal chamber 20b by fasteners, adhesives, or a retention ring as discussed above. As would be appreciated by those skilled in the art, when sleeve member 36 is provided in the compressible configuration described with respect to FIGS. 6 and 7, it is variably adjustable and thus suitable for use with a variety of alternatively sized and shaped containers.

Figure 8:
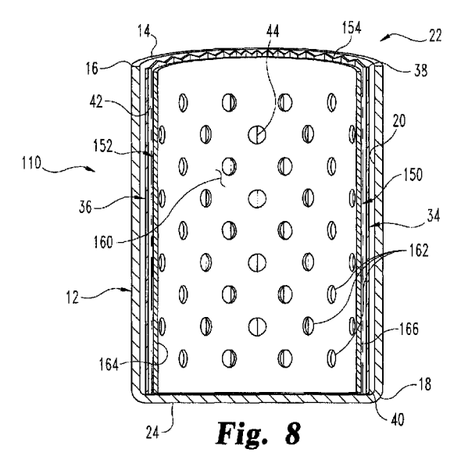
FIG. 8 is a cross-section view of an alternative embodiment container including the desiccant of FIG. 1 and a porous, elongate sleeve member.
Figure 9:
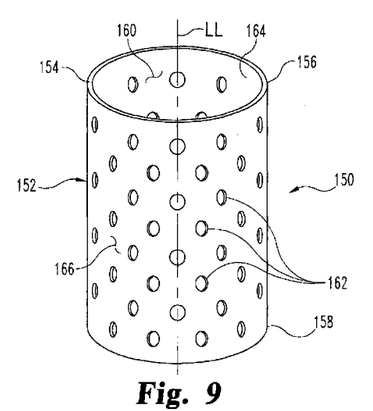
FIG. 9 is a perspective view of the porous, elongate sleeve member positionable in the container of FIG. 8.

An alternative embodiment container 110 is illustrated in cross section view in FIG. 8, where like numerals refer to like features of container 10 previously described. Container 110 is similar to container 10 illustrated in FIG. 3 with sleeve member 36 positioned in internal chamber 20, but further includes a porous sleeve member 150, which is also shown in FIG. 9. Porous sleeve member 150 includes an elongate body 152 having a substantially cylindrical external profile, although it should be appreciated that body 152 may be provided with alternative configurations to correspond with alternative configurations of container 110. Body 152 includes a sidewall 154 that extends along a longitudinal axis LL between a first end 156 and a second end 158. As illustrated in FIG. 8 for example, elongate body 152 is generally sized and shaped to substantially correspond in size and shape to hollow interior 142 of sleeve member 36. For example, body 152 generally extends between first end 16 and second end 18 of external housing 12. However, it should be appreciated that other configurations for body 152 are contemplated.

Porous sleeve member 150 includes a hollow interior 160 that extends between and opens at first and second ends 156, 158 and is laterally surrounded and enclosed by sidewall 154. In one non-illustrated form, it is contemplated that porous sleeve member 150 could be provided with a support surface extending between sidewall 154 that closes second end 158. Hollow interior 160 defines a storage chamber for receiving one or more items stored in container 110, such as one or more test elements 46 for use with a biosensor. A plurality of apertures 162 extend between internal surface 164 and external surface 166 of sidewall 154. Similarly, for the alternative form described above wherein a support surface extends between sidewall 154 at second end 158, it is contemplated that the support surface may also be provided with a plurality of apertures extending therethrough.

As illustrated in FIG. 8 for example, porous sleeve member 150 is removably positionable in hollow interior 42 of sleeve member 36. In one or more non-illustrated embodiments, it is contemplated that porous sleeve member 150 and/or sleeve member 36 could be secured in internal chamber 20 as discussed above, or could be formed integral as a monolithic structure with sleeve member 36. When porous sleeve member 150 is positioned in hollow interior 42, apertures 162 facilitate communication between hollow interior 160 of porous sleeve member 150 and desiccant 34 which is positioned between porous sleeve member 150 and sidewall 14 of external housing 12. In this arrangement, desiccant 34 maintains moisture control relative to items positioned in hollow interior 160 without being positioned in direct contact therewith, thereby eliminating any unintentional interference between the items with interior 160 and desiccant 34.

Figure 10:
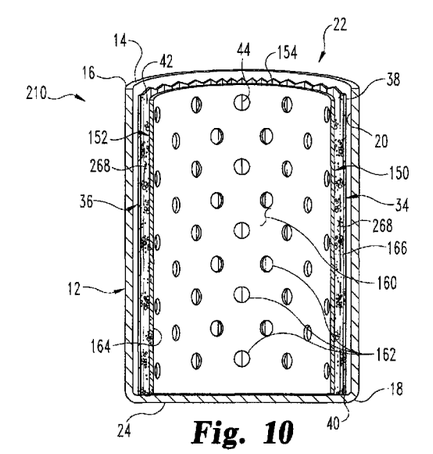
FIG. 10 is a cross-section view of another alternative embodiment container including the desiccant of FIG. 1, a second desiccant and the porous, elongate sleeve member of FIG. 9 positioned therein.

Another alternative embodiment container 210 is illustrated in a cross section view in FIG. 10, where like numerals refer to like features previously described for container 10. Container 210 is substantially similar to container 110 illustrated in FIG. 8, but further includes a second desiccant 268 positioned between hollow interior 160 of porous sleeve member 150 and sidewall 14 of external housing 12. More particularly, second desiccant 268 is positioned in hollow interior 42 between porous sleeve member 150 and elongate sleeve member 36. As illustrated in FIG. 10, desiccant 268 includes a particulate desiccant material in the form of a powder or granule, which may be formed of porous paper, cellulosic fiber, desiccant entrained polymers, porous plastic, molecular sieves, silica gels, clays, starches, calcium sulfate and/or calcium chloride, just to provide a few non-limiting examples. In one form, it is contemplated that desiccant 268 may include two or more desiccant materials which are positioned relative to each other to provide separate regions each having unique drying or moisture control characteristics. For example, desiccant 268 may be configured to provide drying and/or moisture control characteristics adjacent first end 16 of container 210 that are unique relative to drying and/or moisture control characteristics it provides adjacent second end 18 of container 210. However, it should be appreciated that alternative configurations are contemplated.

Apertures 162 facilitate communication between hollow interior 160 of porous sleeve member 150 and desiccants 34, 268 which are positioned between porous sleeve member 150 and sidewall 14 of external housing 12. It should be appreciated that the particulate material of desiccant 268 and apertures 162 extending through porous sleeve member 150 may be sized relative to one another to prevent passage of desiccant 268 into hollow interior 160 of porous sleeve member 150. In another form, it is contemplated that apertures 162 may additionally or alternatively be provided with a screen or mesh material that prevents passage of desiccant 268 into hollow interior 160.

Figure 11:
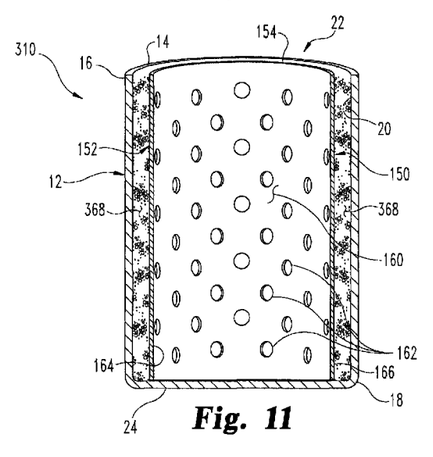
FIG. 11 is a cross-section view of yet another alternative embodiment container including a desiccant and the porous, elongate sleeve member of FIG. 9 positioned therein.

A further alternative embodiment container 310 is illustrated in a cross section view in FIG. 11, where like numerals refer to like features previously described for container 10. Container 310 is provided with a single desiccant and a single sleeve member positioned in internal chamber 20. More particularly, container 310 includes porous sleeve member 150 positioned in internal chamber 20 and desiccant 368 positioned between porous sleeve member 150 and external housing 12. It should be appreciated that porous sleeve member 150 can be sized and shaped similar to internal chamber 20, while also providing a small space between body 152 and external housing 12. Desiccant 368 includes a particulate desiccant material in the form of a powder or granule, which may be formed of porous paper, cellulosic fiber, desiccant entrained polymers, porous plastic, molecular sieves, silica gels, clays, starches, calcium sulfate and/or calcium chloride, just to provide a few non-limiting examples. Apertures 162 facilitate communication between hollow interior 160 of porous sleeve member 150 and desiccant 368. It should be appreciated that the particulate material of desiccant 368 and apertures 162 extending through porous sleeve member 150 may be sized relative to one another to prevent passage of desiccant 368 into hollow interior 160 of porous sleeve member 150. In another form, it is contemplated that apertures 362 may additionally or alternatively be provided with a screen or mesh material that prevents passage of desiccant 368 into hollow interior 160.

Figure 12:
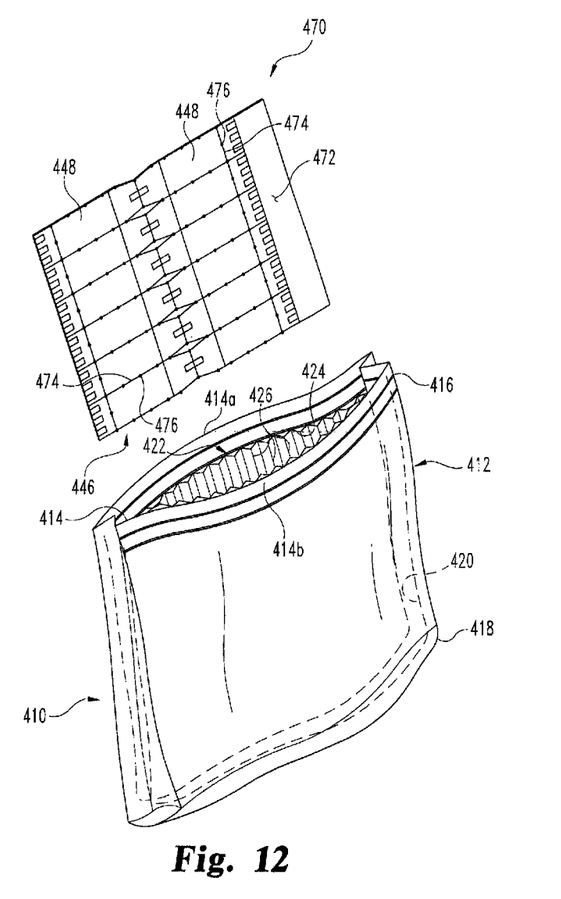
FIG. 12 is a perspective view of another alternative embodiment container including a desiccant.

With reference to FIG. 12, there is illustrated another embodiment container 410. Container 410 is provided as a pouch or bag that includes a resiliently flexible external housing 412 having a sidewall 414 extending between a top portion 416 and a bottom portion 418. Sidewall 414 also surrounds and encloses an internal chamber 420 where one or more items stored in container 410 may be positioned. An opening 422 extends through external housing 412 adjacent top portion 416 and provides access to internal chamber 420. Sidewall 414 includes first and second portions 414a, 414b that extend substantially parallel to one another adjacent top portion 416, and are releasably engageable with one another to close internal chamber 420. For example, in one form, first and second portions 414a, 414b can be provided with a zipper or zipper-lock type arrangement that brings first and second portions 414a, 414b into releasable engagement with one another. However, it should be appreciated that alternative configurations for releasably engaging first and second portions 414a, 414b to one another are contemplated.

Container 410 also includes a desiccant 424 in communication with internal chamber 420 and extending along and lining the interior surface of sidewall 414 between top portion 416 and bottom portion 418. In one form, desiccant 424 may be provided as a removable sleeve member with a corrugated configuration similar to sleeve member 36 described above. Still, in other forms, it is contemplated that desiccant 424 could be secured in internal chamber 420, or could be formed integrally with sidewall 414. In one or more non-illustrated forms, it is contemplated that container 410 may also include another desiccant in addition to desiccant 424. For example, in one particular form, sidewall 414 of external housing 412 could be formed from a desiccant entrained material, although other configurations are contemplated. As illustrated in FIG. 12, desiccant 424 is corrugated and includes a plurality of corrugations 426 extending between top portion 416 and bottom portion 418. However, alternative configurations for corrugations 426 are contemplated. For example, in one non-illustrated form, corrugations 426 may extend orthogonally or obliquely relative to the illustrated configuration. In another non-illustrated embodiment, desiccant 424 may be provided with corrugations 426 that extend only partially between top portion 416 and bottom portion 418. For example, in one form, desiccant 424 may include one or more non-corrugated portions positioned between one or more corrugated portions. Alternatively, desiccant 424 may only be corrugated adjacent top portion 416 or bottom portion 418, although additional configurations are contemplated.

Desiccant 424 is generally formed from or includes one or more desiccant materials, non-limiting examples of which may include porous paper, cellulosic fiber, a desiccant entrained polymer, porous plastic, molecular sieves, silica gels, clays, starches, calcium sulfate and/or calcium chloride, just to provide a few possibilities. In one form, it is contemplated that desiccant 424 may include two or more portions that are formed of separate desiccant materials each having unique drying or moisture control characteristics. For example, in one form, desiccant may be formed of a first desiccant material adjacent top portion 416 and a second desiccant material adjacent bottom portion 418. However, it should be appreciated that alternative configurations are contemplated. Additionally, while not illustrated in FIG. 12, it should be appreciated that container 410 may also be provided with a porous sleeve member in internal chamber 420 to avoid interference between the items stored in container 410 and desiccant 424, similar to the configuration illustrated in FIG. 8. It should also be appreciated that, in other non-illustrated embodiments, container 410 may also be configured similar to the arrangements illustrated in FIGS. 10 and 11, among other alternative configurations, and include a porous sleeve positioned in internal chamber with a corrugated sleeve positioned between the porous sleeve and sidewall 414.

In one form, internal chamber 420 may be sized and shaped to store one or more test elements suitable for use with a biosensor, such as the plurality of test elements 46 described above. It should be appreciated however that other items, in addition to or in lieu of the plurality of test elements 46, may be stored in container 410. In the form illustrated in FIG. 12, a plurality of test elements 446 in the form of electrochemical test strips 448 are arranged together as a unitary test strip card 470 which is removably positionable in internal chamber 420. In one form, card 470 can generally correspond in size and shape to a standard credit card. Card 470 includes a surround area 472 at one end to facilitate movement and positioning thereof by a user. Card 470 also includes perforations 474 in the edges of adjacent test strips 448 and surround area 472 that are only joined at connecting points 476. In this arrangement, each of test strips 448 may be individually removed from card 470 as the need for their use arises. Further details regarding card 470 illustrated in FIG. 12 and other similarly arranged configurations which may be stored in container 410 may be found in U.S. application Ser. No. 12/198,197 entitled "BIOSENSOR TEST STRIP CARDS," the contents of which are incorporated herein by reference in their entirety.

It should be appreciated that the desiccant arrangements described in this document could be utilized by containers in addition to those illustrated, non-limiting examples of which are disclosed in U.S. Pat. Nos. 6,378,702, 6,497,845, 6,534, 017, 6,682,704 and D487,594, the contents of which are incorporated herein by reference in their entirety. The storage containers disclosed herein may also be utilized to store other items related to blood glucose testing, such as lancets for example. However, it should also be appreciated that materials unrelated to blood glucose testing may additionally or alternatively be stored in the containers described herein.

While the invention has been illustrated and described in detail in the drawings and foregoing description, the same is to be considered as illustrative and not restrictive in character, it being understood that only certain embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A container, comprising:
   an external housing including a sidewall extending between a first end and a second end;
   an internal chamber extending between said first end and said second end and surrounded by said sidewall; and
   a resiliently compressible corrugated desiccant in communication with said internal chamber, said desiccant extending along and lining said sidewall between said first end and said second end and applying an expansion force against said sidewall to secure said desiccant in said internal chamber.

2. The container of claim 1, wherein said external housing includes an opening at said first end and a support surface at said second end, said support surface enclosing said internal chamber at said second end.

3. The container of claim 2, wherein said desiccant comprises a sleeve member removably positionable in said internal chamber and formed of a desiccant material.

4. The container of claim 3, wherein said sleeve member is sized and shaped to substantially correspond in size and shape to said internal chamber and extends from said first end to said second end.

5. The container of claim 1, wherein said external housing is resiliently flexible.

6. The container of claim 5, wherein said sidewall includes oppositely positioned first and second portions extending substantially parallel to one another at said first end.

7. The container of claim 6, wherein said first and second portions of said sidewall at said first end are releasably engageable with one another to close said internal chamber.

8. The container of claim 7, further comprising at least one component for use with a biosensor.

9. The container of claim 8, wherein said at least one component includes a plurality of test elements.

10. The container of claim 9, wherein said test elements comprise a plurality of test strips.

11. The container of claim 10, wherein said test strips are coupled together in a unitary arrangement wherein said test strips are individually removable from said unitary arrangement.

12. A container, comprising:
    an external housing extending between a first end and a second end and including a sidewall surrounding an internal chamber; and
    a first desiccant including a corrugated sleeve member removably positioned in said internal chamber and formed of a desiccant material, said corrugated sleeve member being sized and shaped to substantially correspond in size and shape to said internal chamber and including a hollow interior extending between and opening through a first end and an opposite second end.

13. The container of claim 12, wherein said hollow interior is configured for receiving one or more items stored in said container.

14. The container of claim 13, wherein said corrugated sleeve member includes a plurality of corrugations extending along a longitudinal axis.

15. The container of claim 13, further comprising a porous sleeve member positioned in said hollow interior of said corrugated sleeve member.

16. The container of claim 15, wherein said porous sleeve member includes a hollow interior for receiving said one or more items stored in said container.

17. The container of claim 16, wherein said porous sleeve member includes a plurality of openings extending through a sidewall surrounding said hollow interior.

18. The container of claim 15, further comprising a second desiccant positioned between said porous sleeve member and said corrugated sleeve member.

19. The container of claim 18, wherein said second desiccant comprises a particulate material.

20. The container of claim 12, further comprising an opening extending through said first end of said external housing and a cap member coupled to said external housing adjacent to said first end, said cap member being structured to removably cover said opening.

21. The container of claim 12, further comprising at least one component for use with a biosensor.

22. The container of claim 21, wherein said at least one component includes a plurality of test elements.

23. The container of claim 22, wherein said test elements comprise test strips.

24. A container, comprising:
    an external housing including a sidewall extending between a first end and a second end, and said external housing further including a support surface at said second end;
    a storage chamber for receiving one or more items stored in said container and extending between said first and second ends of said external housing and being partially defined by a porous surface including a plurality of apertures extending therethrough, and wherein said support surface forms a boundary to said storage chamber at said second end of said external housing; and
    a first desiccant positioned on said support surface and between said storage chamber and said sidewall of said external housing, wherein said plurality of apertures facilitates communication between said storage chamber and said first desiccant through said porous surface.

25. The container of claim 24, wherein said sidewall of said external housing surrounds an internal chamber and said porous surface is positioned on an elongate sleeve member removably positioned in said internal chamber, said elongate sleeve member including a hollow interior defining said storage chamber.

26. The container of claim 25, wherein said elongate sleeve member and said first desiccant extend between said first and second ends of said external housing.

27. The container of claim 25, wherein said first desiccant comprises a corrugated sleeve member formed of a desiccant material, said corrugated sleeve member extending along a longitudinal axis between said first and second ends of said external housing.

28. The container of claim 27, wherein said corrugated sleeve member includes a hollow interior for receiving said elongate sleeve member.

29. The container of claim 27, wherein said corrugated sleeve member includes a plurality of corrugations extending along said longitudinal axis.

30. The container of claim 27, further comprising a second desiccant positioned between said storage chamber and said sidewall of said external housing.

31. The container of claim 30, wherein said second desiccant is positioned between said elongate sleeve member and said corrugated sleeve member.

32. The container of claim 30, wherein said second desiccant comprises a particulate material.

33. The container of claim 24, wherein said first desiccant comprises a particulate material.

34. The container of claim 24, further comprising at least one component for use with a biosensor.

35. The container of claim 34, wherein said at least one component comprises a plurality of test elements.

36. The container of claim 35, wherein said test elements comprise test strips.

37. A container, comprising:
    an external housing including a sidewall extending between a first end and a second end and surrounding an internal chamber, said internal chamber being closed at said second end by a support surface;
    a porous surface positioned in said internal chamber and extending from said support surface;
    a storage chamber partially defined by said porous surface; and
    a first desiccant positioned between said sidewall and said porous surface.

38. The container of claim 37, further comprising a second desiccant positioned between said first desiccant and said porous surface.

39. The container of claim 38, wherein said first desiccant includes a corrugated sleeve member.

40. The container of claim 38, wherein said second desiccant comprises a particulate material.

* * * * *